Figure 1:
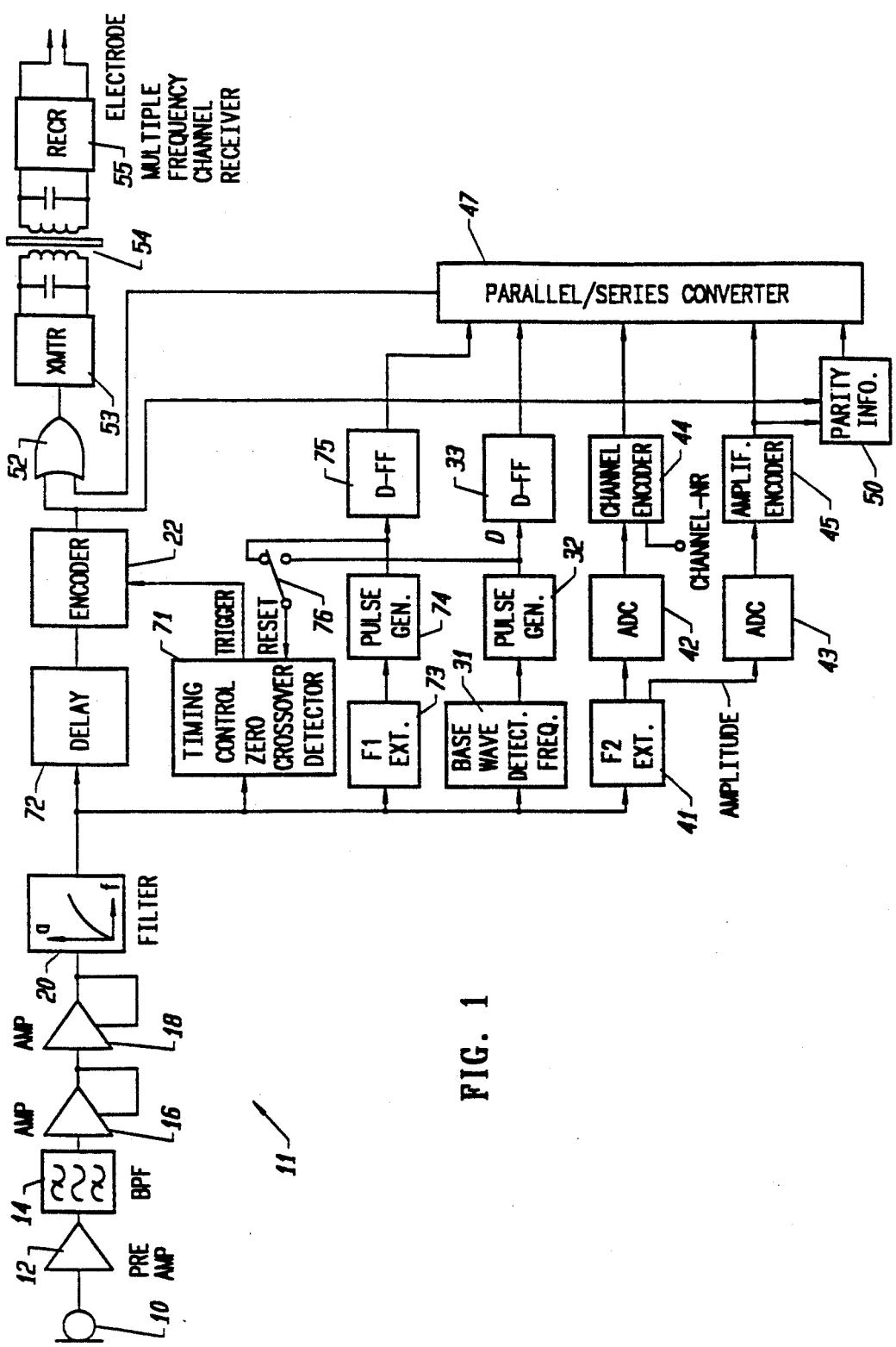

United States Patent [19]
von Wallenberg-Pachaly

[11] Patent Number: 5,215,085
[45] Date of Patent: Jun. 1, 1993

[54] METHOD AND APPARATUS FOR ELECTRICAL STIMULATION OF THE AUDITORY NERVE

[75] Inventor: Ernst-Ludwig von Wallenberg-Pachaly, Berg, Fed. Rep. of Germany

[73] Assignees: Erwin Hochmair; Ingeborg Hochmair, Axams, Austria

[21] Appl. No.: 490,664

[22] PCT Filed: Jun. 22, 1989

[86] PCT No.: PCT/DE89/00415
§ 371 Date: Mar. 1, 1991
§ 102(e) Date: Mar. 1, 1991

[87] PCT Pub. No.: WO90/00040
PCT Pub. Date: Jan. 11, 1990

[30] Foreign Application Priority Data
Jun. 29, 1988 [DE] Fed. Rep. of Germany ....... 3821970

[51] Int. Cl.[5] ............................................. A61N 1/36
[52] U.S. Cl. ................................................. 128/420.6
[58] Field of Search .......................... 128/420.5, 420.6

[56] References Cited

U.S. PATENT DOCUMENTS

| | | | |
|---|---|---|---|
| 3,766,331 | 10/1973 | Zink | 128/420.005 |
| 4,063,048 | 12/1977 | Kissah, Jr. | 128/420.006 |
| 4,267,410 | 5/1981 | Forster et al. | 128/420.006 |
| 4,284,856 | 8/1982 | Hochmair et al. | 128/420.006 |
| 4,390,756 | 6/1983 | Hoffmann et al. | 128/420.005 |
| 4,400,590 | 8/1983 | Michelson | 128/420.006 |
| 4,403,118 | 9/1983 | Zollner et al. | |
| 4,428,377 | 1/1984 | Zoullner et al. | 128/420.006 |
| 4,592,359 | 6/1986 | Galbraith | 128/420.006 |
| 4,593,696 | 6/1986 | Hochmair et al. | 128/420.006 |
| 5,069,210 | 12/1991 | Jeutter et al. | 128/420.006 |
| 5,095,904 | 3/1992 | Seligman et al. | 128/420.006 |

FOREIGN PATENT DOCUMENTS 3016128 11/1981 Fed. Rep. of Germany .
2171605 1/1984 United Kingdom .

OTHER PUBLICATIONS

Konishi, Teruzo, et al., "Effects of Electrical Current Applied to Cochlear Partition on Discharges in Individual Auditory-Nerve Fibers. I. Prolonged Direct-Current Polarization," *The Journal of the Acoustical Society of America*, vol. 47, No. 6 (Part 2) 1970.

Primary Examiner—William E. Kamm
Attorney, Agent, or Firm—Townsend and Townsend

[57] ABSTRACT

A process and device for electrical stimulation of the auditory nerve by a combined pulse and speech resembling analog signal both of which are processed from audio input signals, transmitted to the electrodes in place with the positive amplitude of the dominate portion, i.e., the fundamental frequency of the analog signal.

8 Claims, 2 Drawing Sheets

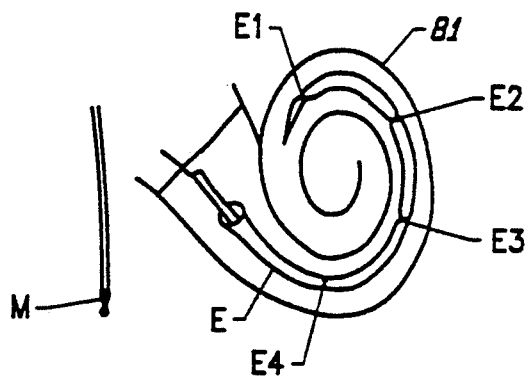
FIG. 2
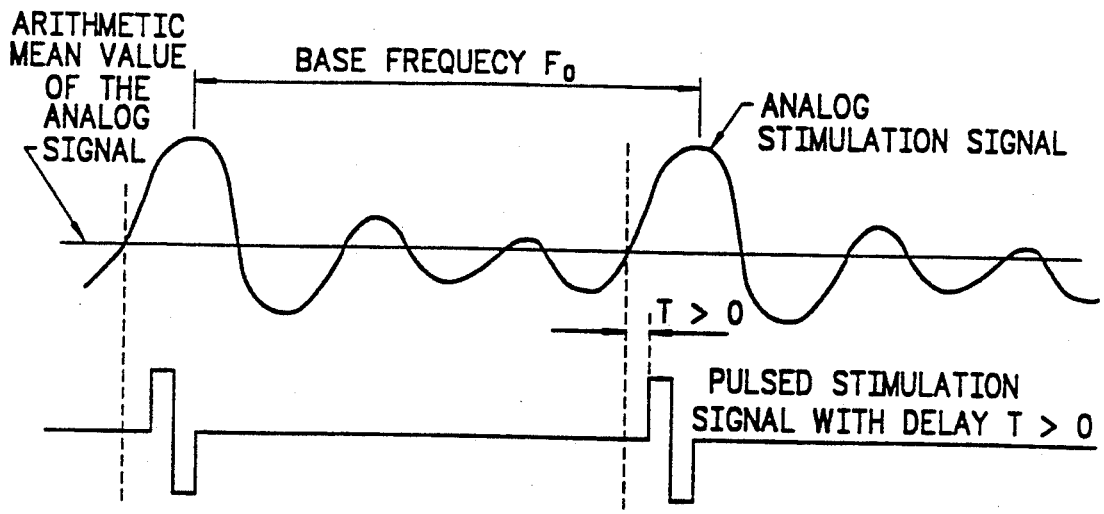
FIG. 3
| CHANNEL | 1 | 2 | 3 | 4 |
|---|---|---|---|---|
| POSITION IN THE COCHLEA | APICAL | | | BASAL |
| SIGNAL | ANALOG | PULSE | PULSE | PULSE |
| CHANNEL SELECTION $F2 \leq 1200$ Hz | | X | | |
| $1200 < F2 < 1800$ Hz | | | X | |
| $F2 \geq 1800$ Hz | | | | X |
FIG. 4

METHOD AND APPARATUS FOR ELECTRICAL STIMULATION OF THE AUDITORY NERVE

The invention relates to a method and an apparatus for electrical stimulation of the auditory nerve in the inner ear, as generically defined by the preamble to the independent claims.

From U.S. Pat. No. 4,593,696, an auditory prosthesis is known with which, via a multi-channel electrode in the cochlea in the inner ear, the auditory nerve is stimulated with a wide-band analog stimulation signal as well as with pulsed stimulation signals or in other words pulse signals, both signals being obtained from audio signals in a speech processor. The analog stimulation signal that is output, via a transmission channel, to an electrode, preferably in the apical region, provides the auditory nerve with the temporal information of the audio signal and thus substantially uses the principle of periodicity of audio signals. However, it was found that certain frequencies are reproduced at specific regions of the cochlea. That is, tonotopic information must also be included in the temporal pattern of the audio signals processed; this is generally known as the locational principle. To enable furnishing this information to the auditory nerve as well, in the known method of U.S. Pat. No. 4,593,696, at least one pulse signal is emitted to the same electrode, or to another electrode which is associated with a different speech parameter. Such speech parameters are the pitch and formants, for instance. These two parameters are also utilized in the known auditory prosthesis, so that pulse signals having the pitch or basic frequency and the frequency of the second formant, for instance, are output to the multiple electrode.

It has now been found that audition is improved, if at all, only slightly with such an additional pulse stimulation. In many cases, further impairment even occurred. Evidently the basic concept of furnishing tonotopic information in addition to the temporal information cannot be reduced to practice by this method. Instead, this kind of simultaneous stimulation of multiple channels creates mutual interference, which can basically be divided into two types: Because of the relatively high conductivity of the fluid in the cochlea, simultaneous multi-channel stimulation causes superimposition of the stimulation currents originating in the various electrodes. On the neuronal level, the excitation patterns originating in individual electrodes are superimposed, even in the case of nonsimultaneous stimulation.

German Patent 30 16 128 discloses a method and an apparatus for generating acoustical speech signals that are intelligible even to the extremely severely hearing-impaired and are intended to furnish high speech intelligibility. The acoustical signals, electrically converted in a microphone and broken down into a plurality of frequency bands by means of filters, that are to be transmitted are used in the form of the envelope curves of the output signals of the filters for modulating alternating voltages associated with the sounds, and these voltages are then carried along with the signals coming from the microphone to the hearer, after amplification. The signals are broken down into at least three frequency bands, and the modulated tones are used along with the total signal of the microphone; both the total loudness and the ratio between the loudness of the modulated tones and that of the original tones are adjusted to a magnitude tolerable to the hearing-impaired person. For voiced sounds, the modulated tones are at least sometimes switched off entirely. It is also possible to implant a hearing aid that is supplied with the prepared signals in wireless fashion. The hearing aid is equipped with a number of electrodes that are associated with the ends of the auditory nerve. In this method and apparatus, essentially only the temporal information of the audio signal is utilized; intelligibility is improved by the special treatment of the voice sounds. In this known device, the transmission of the total speech signal enables the hearing-impaired person to use the speech information available to him directly as well. Often, however, this option is not available to the severely hearing-impaired.

The object of the invention is to further develop the known method and the known apparatus such that in simultaneous stimulation with a wide-band, preferably analog stimulation signal and pulse signals, mutual channel interference does not occur, and temporal information and tonotopic information can be furnished to the hearing-impaired person, to improve audition.

This object is attained in accordance with the invention by the characteristics recited in the independent claims.

Accordingly, as before, one electrode of the implanted multiple electrode is supplied with a preferably analog, wide-band stimulation signal, the curve shape of which is similar to the speech signal. This stimulation signal essentially furnishes the temporal information. Another electrode is supplied, via a further channel, with at least one pulse signal having a frequency that is equivalent to the frequency of a dominant component in the speech signal, generally the basic frequency. This pulse signal is transmitted in phase with the positive amplitude of the fundamental wave. If an analog stimulation signal is used, then the pulse signal is transmitted during the positive leading edge of the dominant primary wave of the speech signal, between the zero crossover and the maximum of the positive amplitude. The electrodes are wired to the implanted receiver in such a way that a positive amplitude of the stimulation signals makes the active electrode negative, or in other words generates a stimulus. This applies to both the analog and the pulse signals. The pulse signal is output to an electrode that stimulates nerve fibers of the auditory nerve in the cochlea of the inner ear that are sensitive to the tonotopic information that is to be emphasized by the pulse signals. In principle, the most favorable solution would be to select an electrode that is located directly in the vicinity of such nerve fibers that are sensitive to the frequency to be emphasized of the speech parameter to be emphasized. However, at least so far, this is not possible in practice because the stimulation electrode can be introduced properly only to a maximum of one winding deep, beginning at the base of the cochlea. Although with a multi-channel electrode the tonotopic disposition of the nerve fibers can be utilized, it must be assumed that nerve fibers that are sensitive to higher frequencies in a person with normal hearing are stimulated. Even so, as a result of the pulse stimulation, patients with an auditory prosthesis according to the invention describe the desired tonal perception for substantially lower pitches. By testing the patient, it can be found which electrode must be selected in order to attain the desired pitch perception.

Naturally more than one pulse signal can also be transmitted simultaneously with the preferably analog stimulation signal, these pulse signals then being associated with different speech parameters. For instance, if pulses for emphasizing the first and second formants are transmitted simultaneously with the analog signal, this is done in each case with the fundamental frequency or some other dominant frequency, for instance that of the first formant, of the speech signal. In the method, not only the location of the pulses, but also the group transit time of the speech processor, which is dependent on the frequency, and under some circumstances the electrode impedance will of course be taken into account. The amplitude response and phase response of these transmission elements, which vary from one patient to another, can be simulated with digital filters. The fundamental frequency can for instance also be extracted with digital filters.

In experiments using a quadruple electrode, it was possible to demonstrate that the auditory system is capable of logically combining the temporal information transmitted by the analog wide-band signal and the tonotopic information transmitted by the pulse channels. The patients report that the auditory impressions were clearer and more natural as a result of the additional tonotopic information. The mutual interference of the various information channels can be reduced sharply because the pulse rate of the pulse signals was equivalent to the periodicity of a dominant component, preferably the fundamental wave of the analog stimulation signal. In all cases studied, an improvement in recognition of the second formant and thus an improvement in the overall result of vocal identification occurred. The perception of the speech characteristics transmitted by the analog stimulation signal was not impaired at all and was markedly improved by the purposeful pulse stimulation. It can be assumed that even better results will be attained if a multiple electrode having more than four electrodes is used. Multiple electrodes of this kind that have up to 22 channels are already known.

As pulse signals, biphase signals are preferably used. In the adaptation, these biphase pulses were always at the zero crossover of the primary wave of the analog stimulation signal and had the same polarity. If the phase displacement of the analog stimulation signal of an average of approximately 60° caused by the electrode is taken into account, then the pulses at which the phase displacement is negligible were located approximately in the upper third of the positive leading edge of the analog stimulation signal, as called for above. The electrodes were wired to the implanted receiver in such a way that a positive amplitude of the stimulation signal makes the active electrode negative or in other words generates a stimulus. The amplitude of the pulse signals is adjusted such that when the pulse signal is additionally switched to another channel, a change in the timbre is produced without a substantial increase in loudness; the amplitude of the analog stimulation signal remained unchanged. The loudness of the pulse channel alone was usually only very slight in comparison with the loudness of both channels together. The pulses are most effective when they occur at the maximum of the analog stimulation signal or shortly before that. This is also confirmed by the fact that an excessive delay in the pulses beyond the maximum of the analog stimulation signal makes them ineffective.

When the pulse signals are located at the maximum of the analog stimulation signal or shortly before that, the action potentials of the analog stimulation channel occur approximately simultaneously with those of the pulse stimulation channel, thereby precluding interference from temporal interaction of the action potentials.

The combination of a preferably analog stimulation signal on one channel and at least one pulse signal on another channel—which is selectable from an arbitrary number of additional channels—requires comparably low power, making implementation of this strategy into an integrated circuit for the auditory prosthesis possible. By a suitable selection of the parameters of pulse duration, pulse amplitude, pulse rate and phase relation of the pulses, the influences of current propagation in the cochlea, with simultaneous multi-channel stimulation, are taken into account for the first time in this method. The advantage of the proposed method is also that either the analog stimulation channel or the pulse channels can also be used alone, independently of one another. This makes it possible to adapt the capacities of the patient's auditory system individually in terms of the complexity of the stimulation pattern. One of these options would for instance be to use the frequency of the first formant for selecting the channel of the pulse signal, if this formant cannot be reliably recognized using the periodicity principle. By purposeful utilization of the principles of periodicity and location, it is also possible, among other goals, to drive all the channels with pulse signals; in that case the individual components of the signal transmitted, for instance including the first and second formant, among others, are furnished, each with the fundamental frequency, to different electrodes.

The invention is described in further detail in an exemplary embodiment, referring to the drawing. Shown are:

FIG. 1, a block circuit diagram of an auditory prosthesis according to the invention;

FIG. 2, a schematic illustration of the cochlea of the inner ear, with a stimulation electrode having four channels;

FIG. 3, an illustration of an analog stimulation signal and a pulsed stimulation signal for simultaneous stimulation; and FIG. 4, an overview of the channel selection in simultaneous stimulation with an analog stimulation signal and a pulsed stimulation signal.

The block circuit diagram in FIG. 1 shows an auditory prosthesis having a speech processor 11, which has a microphone 10, a preamplifier 12, a bandpass filter, two regulated amplifiers 16 and 18 for amplification adjustment, and a filter network 20. In the bandpass filter 14, the audio signal received from the microphone 10 and amplified is limited to a bandwidth of between approximately 150 Hz and 6 kHz, which is necessary for speech transmission. In the amplifier 16, the sensitivity is adjusted by means of an automatic gain stabilizer, and in the syllable compressor 18 the amplitude ratio of consonants to vowels is increased. In the filter network 20, the processed signal is adjusted such that all the frequencies within the frequency band sound approximately equally loud.

Next, the processed signal is further processed in parallel in a plurality of circuits paths.

In a first path, the analog signal is first carried via a delay circuit 72, in which the fundamental wave of the speech signal is delayed by approximately one period. This signal is delivered to an encoder 22, for instance an adaptive delta modulator, the output of which is connected to an OR gate 52. Via this first channel, an analog, wide-band stimulation signal is made available.

The signals for the pulse stimulation are likewise developed from the speech signal.

In one circuit path, a fundamental wave detector 31, a pulse generator 32 and a D flip-flop 33 are provided, so that the frequency for the pulse stimulation is determined on this path. The second formant F2 is determined in a circuit 41. The frequency of the second formant F2 is delivered to a channel encoder 44 via an analog/digital converter 42. The amplitude of the second formant is delivered to an encoding circuit 45 via an analog/digital converter 43. The channel number defines the location of each one of four electrodes E1-E4 of a stimulation electrode E, as will be explained below in conjunction with FIGS. 2-4.

The outputs of the circuits 33, 44 and 45 are delivered to a parallel/serial converter 47 and from there are carried to the second input of the OR gate 52.

In a circuit 50 for parity control, the composite signal is checked again.

The circuit elements described thus far are equivalent in function to those of the aforementioned U.S. Pat. No. 4,593,696.

In addition to the circuit elements described above, a timing control 71 is also provided, which is embodied as a sample and hold circuit. In this circuit 71, the zero crossover of the primary wave of the analog stimulation signal is detected.

A parallel circuit path is also provided, with a circuit 73 for extracting the first formant F1, which is connected to a series circuit comprising a pulse generator 74 and a further D flip-flop 75. The output of the D flip-flop is carried to the parallel/serial converter 47. The timing control 71 can be reset either via the pulse generator 32 or via the pulse generator 74; the selection as to this reset operation is done with the aid of a switch 76. The timing control 71 triggers the encoder 22; as a result, an exact temporal relationship is attained between the analog stimulation signal and the pulsed stimulation signal, either as a function of the fundamental frequency or under some circumstances the frequency of the first formant.

The combined signal derived from the analog stimulation signal and the pulsed stimulation signal is fed inductively, via a transmitter 53, to a receiver 55 in the inner ear, which is connected in turn to the stimulation electrode E.

As shown in FIG. 2, this stimulation electrode E is inserted into the cochlea 81 of the inner ear and has four active electrodes and channels E1, E2, E3 and E4. The electrodes are embodied as bipolar or unipolar, in the conventional manner. In the unipolar configuration, an active electrode E1, E2, E3, E4 is stimulated counter to a remote ground electrode M, located for instance under the temporal muscle. The electrode E1 is located at the apical end and the electrode E4 at the basal end of the cochlea 81. The electrodes 2 and 3 are disposed at intervals between these two electrodes.

In FIG. 3, the top line shows the analog stimulation signal, which fluctuates about an arithmetic mean value; the spacing of adjacent dominant amplitudes defines the fundamental frequency F0. This analog stimulation signal is typically transmitted to the electrode E1, that is, via the channel 1; see FIG. 4. The electrodes are wired to the implanted receiver in such a way that a positive amplitude of the stimulation signals shows in FIG. 3 makes the active electrode negative (or cathodic) or in other words generates a stimulus.

The pulsed stimulation signal shown in the second line of FIG. 3, which is associated with the second formant F2, is likewise transmitted with the fundamental frequency F0, to one of the electrodes E2, E3 or E4, as shown in FIG. 4, via a respective one of the channels 2, 3 and 4, depending on the actual frequency ascertained in the circuit 41. The pulsed stimulation signal in this case is a biphase signal, which is transmitted in each case during the rising positive edge of the fundamental wave between its zero crossover and the maximum. The electrodes are wired to the implanted receiver in such a way that the positive amplitude of the stimulation signals shown in FIG. 3 makes the active electrode negative (cathodic), or in other words generates a stimulus. If the second formant, for instance, has a frequency of less than or equal to 1200 Hz, then this pulsed stimulation signal is delivered to the electrode E2 via the second channel. If the frequency is between 1200 and 1800 Hz, the stimulation is effected via the third channel and the electrode E3. If the frequency is above 1800 Hz, then the electrode E4 is stimulated via the fourth channel. The selection of the frequency range and of the number and disposition of electrodes is by way of example. In some cases, the analog stimulation signal can for instance also be delivered to the electrode E2, so that in that case the electrode E1 is acted upon by a pulsed stimulation signal, for example. The selection of the individual channels and hence of the electrodes can be optimally adapted from one patient to another in this way.

The pulse duration is typically between 200 microseconds and 2.5 milliseconds, depending on the threshold of the pulse-transmitting channel; preferably, the shortest possible pulse durations are used. The amplitude of the pulsed signals is adjusted such that in simultaneous stimulation of the analog channel and the pulse channels, the switchover within the pulse channels varies the perception, with no change or an only slight change in loudness, but produces a change in the pitch impression.

It is also entirely possible to emphasize other speech parameters with corresponding pulsed stimulation, so that a plurality of pulsed stimulation signals are also transmitted to correspondingly different electrodes. For markedly improved audition, however, recognition of the second formant F2 is a first requirement.

The auditory prosthesis described can be used very flexibly and can be adapted to different needs of the particular patient. The analog wide-band channel is always stimulated. However, modifications of the stimulation described are possible. For instance, a purely pulsed stimulation with pulses of fundamental frequency F0 and pulses of the formants F1 and F2 is possible, with the superposition of these pulses being in phase again, in order to attain the desired goal. The stimulation frequency for the pulse channels is typically the fundamental frequency F0 or the frequency of the first formant F1. The channel selection for the pulse channels can be done as a function of the first formant F1, the second formant F2, or the natural frequency of the anterior articulation tract. Furthermore, two pulse channels can be stimulated in alternation, with the stimulation via a first channel being done as a function of the first formant in one phase and as a function of the second formant or the natural frequency in the other phase. The channels that transmit the information pertaining to the first formant should then be disposed in the middle between the analog channel and the basally connected channels, which are used for the information pertaining to the second formant.

I claim:

1. Apparatus for electrical stimulation of the auditory nerve in the inner ear comprising
   a speech processor for generating an analog signal from an audio signal,
   first circuit means for generating at least one pulsed stimulation signal from the audio signal for emphasizing at least one speech parameter including a second formant of said audio signal,
   a stimulation electrode for location in the cochlea of the inner ear including a plurality of active electrodes locatable at different sites in the cochlea,
   second circuit means for transmitting said analog signal and said at least one pulsed stimulation signal to said stimulation electrode and said plurality of active electrodes via a plurality of channels, and
   third circuit means for determining frequency, zero crossover, and first positive maximum of a fundamental wave of said audio signal, said third circuit means providing timing control for transmission of said pulsed signal during a positive leading edge of said fundamental wave.

2. Apparatus as defined by claim 1 wherein one of said channels carries pulsed signals as a function of said second formant, and further including means connecting said one of said channels to one of said active electrodes for stimulating nerve fibers of the auditory nerve that are sensitive to the tonotopic information to be emphasized by said pulsed signal.

3. A method of electrical stimulation of the auditory nerve in the inner ear comprising steps of
   generating an analog stimulation signal from an audio signal,
   generating at least one pulsed stimulation signal from said audio signal corresponding to a second formant of said audio signal,
   providing a stimulation electrode in the cochlea of the inner ear including a plurality of active electrodes located at different sites in the cochlea, and
   transmitting said analog stimulation signal and said at least one pulsed stimulation signal to said active electrodes via a plurality of transmission channels, including transmitting said analog stimulation signal to an apical active electrode and transmitting said pulsed signal to an active electrode at a frequency that is equivalent to a dominant component of the analog stimulation signal, with said pulsed signal being in phase with a positive amplitude of said dominant component, whereby a positive amplitude of the stimulation signals makes the active electrodes negative and generates a stimulus.

4. The method as defined by claim 3 wherein said step of transmitting said analog stimulation signal and said at least one pulsed stimulation signal includes transmitting said pulsed stimulation signal in the vicinity of a positive leading edge of a dominant primary wave of said analog signal between a zero crossover and a maximum of the positive amplitude of said analog signal.

5. The method as defined by claim 3 wherein said step of transmitting includes transmitting said pulsed stimulation signal at a frequency corresponding to a fundamental wave of said audio signal.

6. The method as defined by claim 3 wherein said step of transmitting includes transmitting said pulsed stimulation signal to active electrodes for stimulating nerve fibers of the auditory nerve in the cochlea of the inner ear that are sensitive to tonotopic information emphasized by said pulsed signal.

7. The method as defined by claim 3 wherein said step of generating at least one pulsed stimulation signal includes generating biphase pulses having an initially positive and then negative amplitude wherein a positive amplitude of the pulsed signal makes the active electrode negative and generates a stimulus.

8. The method as defined by claim 3 wherein said step of generating an analog stimulation signal includes adjusting said analog stimulation signal in terms of pleasing loudness, and said step of generating at least one pulsed stimulation signal includes adjusting amplitude of said at least one pulsed stimulation signal such that a variation in timbre is produced without a substantial increase in loudness.

* * * * *